United States Patent [19]

Deacon

[11] Patent Number: 4,822,360

[45] Date of Patent: Apr. 18, 1989

[54] INFLATABLE, INTRAOCULAR LENS AND METHOD OF IMPLANTING THE LENS IN THE CAPSULE OF AN EYE

[75] Inventor: Jim Deacon, Capistrano Beach, Calif.

[73] Assignee: University of Utah, Salt Lake City, Utah

[21] Appl. No.: 169,231

[22] Filed: Mar. 16, 1988

[51] Int. Cl.$^4$ .......................... A61F 2/16; A61B 17/00
[52] U.S. Cl. ...................................... 623/6; 128/303 R
[58] Field of Search ......................... 623/6; 128/303 R

[56] References Cited

U.S. PATENT DOCUMENTS

| 4,373,218 | 2/1983 | Schachar | 623/6 |
|---|---|---|---|
| 4,585,457 | 4/1986 | Kalb | 623/6 |
| 4,619,662 | 10/1986 | Juergens, Jr. | 623/6 |
| 4,681,102 | 7/1987 | Bartell | 623/6 |
| 4,685,921 | 8/1987 | Peyman | 623/6 |
| 4,693,717 | 9/1987 | Michelson | 623/6 |

Primary Examiner—Ronald L. Frinks
Attorney, Agent, or Firm—Thorpe, North & Western

[57] ABSTRACT

An inflatable, intraocular lens is disclosed for implanting within the lens capsule of an eye following removal of the biological contents of the lens capsule. The lens comprises a thin-walled lens skin forming a substantially enclosed, collapsible sac made of a flexible polymeric material and having a wall thickness no greater than about 0.15 millimeter. The lens skin further has an exterior shape when inflated which is substantially the same as the shape of the biological content of the lens capsule of a normal eye. A pair of longitudinal, flexible tubes extend from the lens skin, with the lumen of each tube communicating with the inside of the sac formed by the lens skin. In a collapsed, folded condition, the lens skin can be inserted into the lens capsule of an eye through a relatively small incision in the eye, with the lens skin being adapted for inflation through the pair of tubes after the lens skin has been inserted into the lens capsule of the eye. The lens skin is filled with a liquid which will cure to an elastomeric material having proper optical qualities. An insertion device, a method of inserting and filling the lens skin with a liquid capable of curing to form a proper elastomeric material, and an instrument for aiding in removing bubbles from the inflated lens skin during the filling procedure are also disclosed.

12 Claims, 3 Drawing Sheets

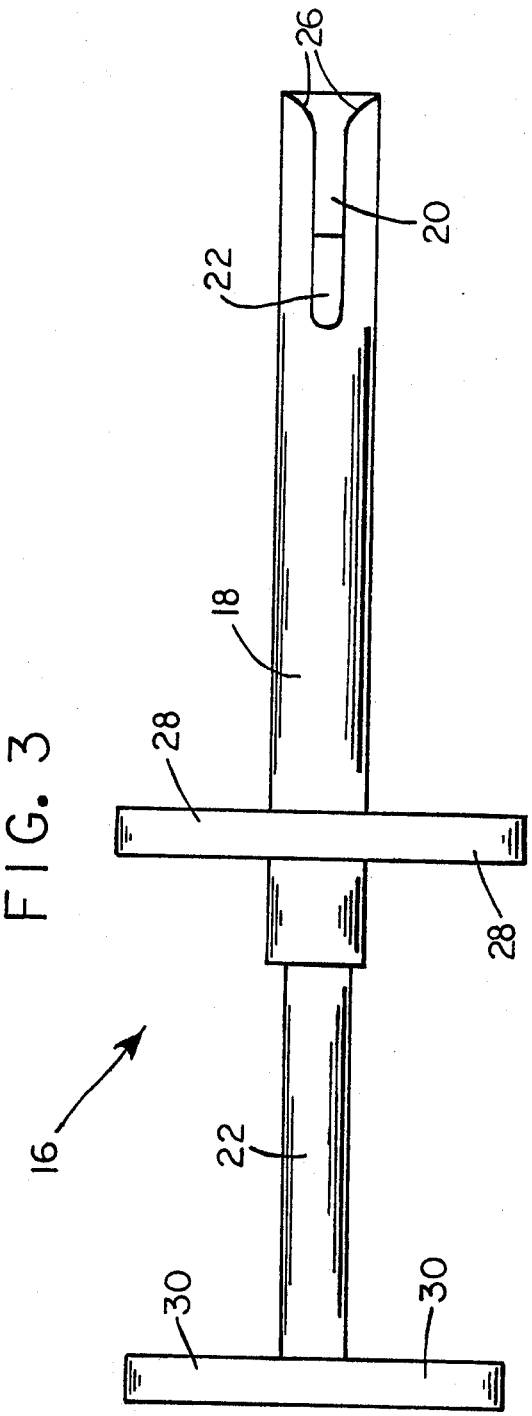
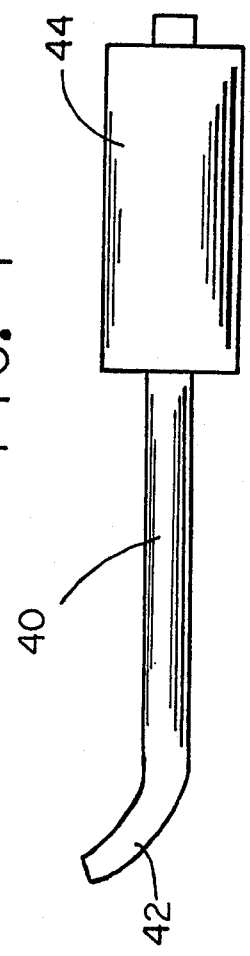
FIG. 3
FIG. 4

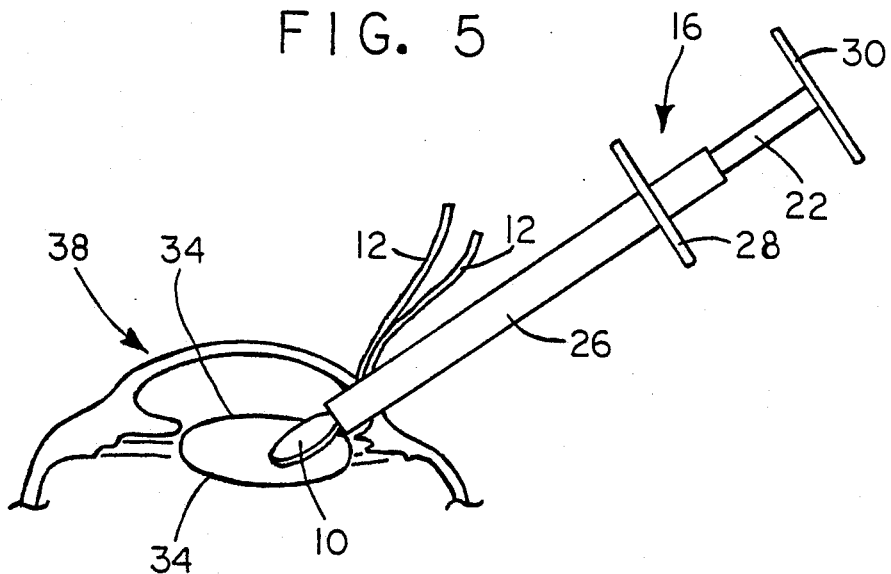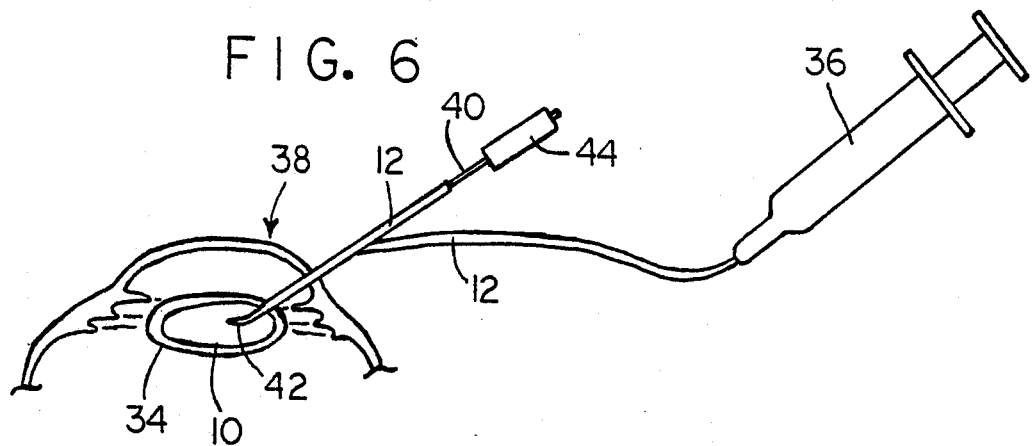

INFLATABLE, INTRAOCULAR LENS AND METHOD OF IMPLANTING THE LENS IN THE CAPSULE OF AN EYE

BACKGROUND OF THE INVENTION

1. Field of the Invention

The present invention relates generally to an intraocular lens for implanting within the lens capsule of an eye following the removal of the biological contents of the lens capsule. The present invention further relates to apparatus and the method of implanting the novel lens in the lens capsule of an eye.

2. State of the Art

Cataract is a common ailment effecting the human eyes, especially the eyes of older people. Cataract is in fact the most common cause of blindness. Removal of the clouded biological lens material of the affected eye will restore light perception, but full rehabilitation requires that the refractive power of the natural lens be replaced by some other means.

In the somewhat distant past, the replacement of the refractive power of the natural lens was achieved by the use of spectacles and contact lenses. However, both spectacles and contact lenses have limitations. Spectacles produce major optical distortions, and patients, especially older people, have a difficult time adjusting to the various problems involved in wearing and caring for contact lenses.

Current state of the art practice in cataract surgery includes the implanting of an artificial lens in the eye to mimic the function of the original, natural lens. The artificial lenses are referred to as intraocular lenses, and more than 900,000 are implanted in the United States each year. The most common procedure involves the placement of a rigid plastic lens in the eye of the patient following the removal of the natural, biological lens material.

There are problems associated with the use of rigid plastic lenses. The hard plastics used can erode into delicate ocular tissues, leading to medical complications. The accommodative, or focusing capability of the eye is completely lost inasmuch as normal accommodation is effected by deformation of the biological lens. Rigid plastic lenses can not deform and therefor have no provision for accommodation. Further, the rigid plastic lenses require that a relatively large incision be made for their insertion into the eye. This results in extended post-operative recovery times and increased risk of induced corneal astigmatism when compared with surgery involving smaller incisions.

There has been developed a surgical procedure called phacoemusification which allows the biological lens material to be removed through a relatively small incision of as little as 3 millimeters in comparison to incisions in the range of 7 to 11 millimeters that are required for the insertion of a rigid plastic lens into the eye. Other surgical procedures to remove lens material through small incisions are presently being developed. It has been proposed to make the replacement lens from a compressible material which can be inserted into the eye through the smaller incision.

In U.S. Pat. No. 4,619,662 an intraocular lens is disclosed which consists of a preformed, molded mantle having substantially thick side walls of a preformed shape and size. It is taught that the preformed sidewalls contain at least 30% of the volume of the lens. The preformed, molded lens has a single cannula extending therefrom. In use, the air is evacuated from the interior of the preformed mantle through the cannula to collapse the mantle for insertion into the eye through the incision in the eye. The lens of U.S. Pat. No. 4,619,662 is designed to be positioned in the posterior or anterior chamber of the eye. There is no suggestion of positioning the lens within the lens capsule of the eye.

The collapsed, molded mantle of U.S. Pat. No. 4,619,662 is inserted into the eye using the cannula, and once the mantle is within the eye, additional polymer material is then injected into the lens through the cannula to fill the void volume of the molded mantle. Once the lens is filled, the cannula is incised from the lens. There are no means provided for flushing the lens to remove small air bubbles attached to the interior surface of the molded mantle following the filling of the void volume with the polymeric material. In fact, there is no recognition of such a problem with residual air bubbles, and there is no suggestion, of course, as to a means of eliminating the residual air bubbles.

3. Objectives

A principal objective of the invention is to provide a surgeon with a novel intraocular lens system, with means and method of implanting the lens within the lens capsule of an eye.

A particular objective of the invention is to provide such a lens system wherein the lens comprises a very thin-walled skin forming a substantially enclosed, collapsible sac such that the lens skin can be folded into a small size which can be inserted into the lens capsule of an eye through a small incision being no larger than 3 or 4 millimeters, and further wherein a pair of longitudinal, flexible tubes extend from the lens skin, with the lumen of each tube communicating with the inside of the sac formed by the lens skin and with the tubes being adapted to extend from the eye through the incision following the insertion of the collapsed, folded, thin walled sac into the lens capsule of the eye.

An additional objective of the present invention is to provide means and a method for inflating the sac formed by the lens skin after the folded lens skin has been placed within the lens capsule of the eye and for removing residual air bubbles from the inflated sac, wherein a liquid is injected through one of the tubes extending from the sac to inflate the sac, with additional fluid then being flushed through the sac and out the other one of the tubes extending from the sac to expel air bubbles from the sac.

Another objective of the present invention is to provide such a novel intraocular lens system in which the liquid used to fill the lens skin within the lens capsule of the eye is adapted to form a clear, resilient elastomer, wherein the artificial lens formed by the skin and the filling closely mimics both the dimensions and the compliance of a natural, biological lens, so that the ciliary apparatus of the eye is able to deform the artificial lens in the same manner it does a natural, biological lens to provide accommodation with the artificial lens.

BRIEF DESCRIPTION OF THE INVENTION

The above objectives are achieved in accordance with the present invention by providing a novel, unique lens system for implantation within the lens capsule of a patient's eye following the removal of the impaired, biological contents of the lens capsule. The lens system comprises a thin-walled lens skin which forms a substantially enclosed, collapsible balloon or sac. The lens skin is made of a clear, flexible polymeric material and has a wall thickness no greater than about 0.15 millimeters. The lens skin further has an exterior shape when inflated which is substantially the same as the shape of the biological content of the lens capsule of a natural eye.

A pair of longitudinal, flexible tubes are provided to extend from the lens skin. The lumen of each tube communicates with the inside of the sac formed by the lens skin. In accordance with the invention, the lens skin, when in a collapsed, folded condition, is inserted into the lens capsule of the eye using a novel injector which will be described fully hereinafter. The folded lens skin can be inserted through a relatively small incision of no more than 3 or 4 millimeters, and the lens skin is adapted to be inflated through the pair of tubes after the lens skin has been inserted into the lens capsule of the eye.

The pair of tubes extend outwardly from the implanted lens skin through the small incision in the eye. The sac or balloon formed by the lens skin is inflated and filled with a clear elastomeric material. The elastomeric material is injected through one of the pair of tubes in the form of a flowable, liquid, polymerizable material which can be polymerized or cured in the filled lens skin to form a stable gel or elastomeric material having the desired optical qualities. Any air which may be contained in the lens skin as it is being filled is expelled through the other one of the pair of tubes.

Residual air bubbles can be flushed from the inflated lens skin following its inflation by introducing additional liquid into the lens skin through the first or filling tube and expelling an equivalent amount of fluid from the second or discharge tube. A bubble evacuating probe is advantageously provided which can extend through the second tube into the inflated lens skin. The probe is used to dislodge small air bubbles from the inside surface of the inflated lens skin while the additional liquid is being flushed through the inflated lens skin. The dislodged air bubbles are flushed from the inflated lens skin with the ejection of the excess liquid from the discharge tube.

When the inflated lens skin is properly filled with fluid and all air bubbles have been evacuated from the inflated lens skin, the pair of tubes are clamped. The liquid material in the inflated lens skin is allowed to polymerize or cure, and the pair of tubes are then carefully cut and removed from the inflated surface of the lens skin.

Additional objects and features of the invention will become apparent from the following detailed description, taken together with the accompanying drawings.

THE DRAWINGS

A preferred embodiment of the present invention representing the best mode presently contemplated of carrying out the invention is illustrated in the accompanying drawings in which:

FIG. 3 is a top view of an injector in accordance with the present invention which is advantageously used to insert the folded lens skin into the lens capsule of an eye;

FIG. 4 is an elevational view of an evacuation probe in accordance with the present invention;

FIG. 5 is a schematic cross section through an eye showing the injector of FIG. 3 being used to insert a folded lens skin within the lens capsule of the eye; and FIG. 6 is a schematic cross section through an eye showing the injected lens skin in place with the evacuation probe being used to dislodge air bubbles so that they can be flushed from the inflated lens skin.

DETAILED DESCRIPTION OF THE ILLUSTRATED EMBODIMENTS

Figure 1:
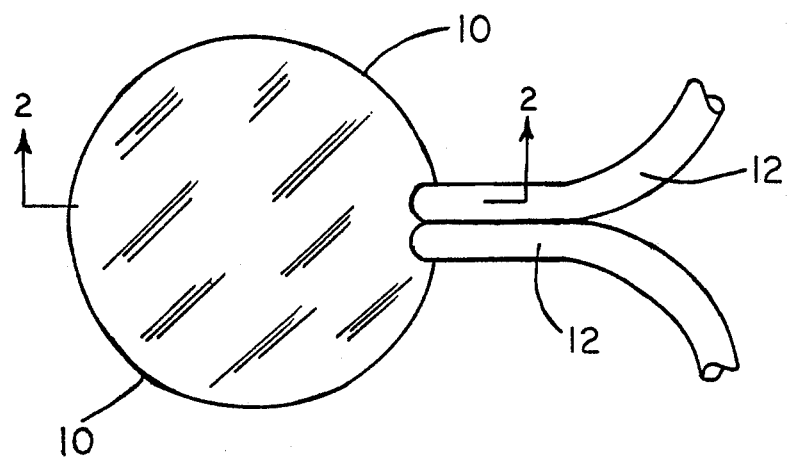
FIG. 1 is a top view of the lens skin and associated pair of tubes in accordance with the present invention, showing the lens skin in its inflated condition.
Figure 2:
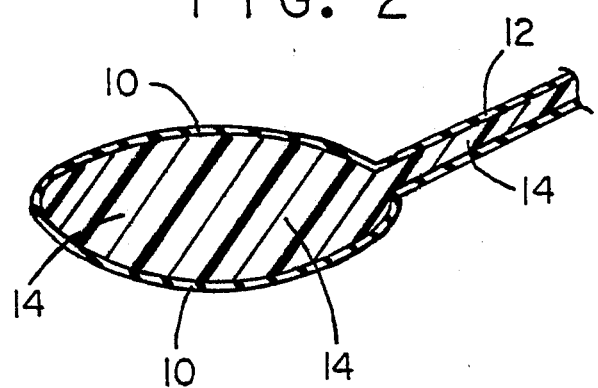
FIG. 2 is a cross section of the lens skin and pair of tubes of FIG. 1 taken along line 2—2 of FIG. 1.

Referring to the drawings, there is shown in FIGS. 1 and 2 an inflatable, intraocular lens in accordance with the present invention which is designed to be implanted within the lens capsule of an eye following removal of the impaired biological contents of the lens capsule. The lens comprises a thin-walled lens skin 10 forming a substantially enclosed, collapsible sac which is shown in FIGS. 1 and 2 in its inflated shape In its inflated shape, the lens skin 10 is sized to essentially fill and fit firmly within the lens capsule of an eye, with the lens skin having substantially the same shape as the biological lens material normally contained in the lens capsule of the eye but which has been removed for medical reasons.

The lens skin 10 is made of a clear, flexible polymeric material and has a wall thickness of no more than about 0.15 millimeters and generally between about 0.04 and 0.15 millimeters. The polymer can be a silicone material as presently used in commercial intraocular lenses or other polymeric material such as polyurethane. The wall thickness can be varied over the area of the skin to control the deformation of the artificial lens.

A pair of longitudinal, flexible tubes 12 are provided extending from the lens skin 10, with the lumens of each of the tubes 12 communicating with the inside of the sac formed by the lens skin 10. Each of the tubes 12 can have an internal diameter of between about 0.40 and 1.5 millimeters and preferably between about 0.85 and 1.15 millimeters. The length of the tubes 12 can vary considerably. The tubes 12 must only be of sufficient length to extend outwardly of the eye from the incision in which lens skin is inserted into the lens capsule of the eye. As a practical matter, the length of the tubes 12 will generally be at least about 2.5 centimeters or greater.

The lens skin 10 and the attached tubes 12 can be made by several methods well adapted for forming such balloon type structures. During development of the present invention, the lens skin 10 and attached tubes 12 were made by first forming a wax mold with steel wires extending therefrom. The steel wires provided the forms for the pair of tubes 12. The wax mold had the shape of the normal, biological lens material contained in the lens sac of an eye, and the steel wires were inserted into the wax mold near the equator and angling upwardly at about 15 degrees from the equatorial plane of the wax mold. The wax mold and at least a portion of the steel wires were then dipped into a solution of the polymer used to form the lens skin 10 and integrally attached tubes 12.

Immediately after each dipping, the form was placed in a ventilated oven at about 55° C. for a minimum of 30 minutes to evaporate the solvent. Orientation of the form was alternated during evaporation to produce reasonably consistent wall thicknesses, with the greatest deposition at the bases of the ports. Typically, three dippings were made and then the form was left to cure in the oven for about 24 hours. This resulted in an average wall thickness of about 0.07 millimeters at the centers of the optical surfaces and about 0.08 millimeters at the equator of the resulting lens skin. After curing, the steel forms were removed and the wax was evacuated by heating the article to approximately 130° C. in an oven until the wax melted, and the melted wax was then removed from the lens skin 10 and pair of tubes 12 by squeezing the molten wax from the pair of tubes 12.

It is to be noted that the lens skin 10 and the pair of tubes 12 could be formed as separate items. One-way valves could be formed in the lens skin as it is being formed. Such valves would work on the same principle as the leaves in the human heart, snapping shut in response to back flow. The tubes 12 could be inserted into the valves and would be held by the tension of the leaves of the valves or by a cement.

The lens skin 10, when in a collapsed, folded condition, can be inserted into the lens capsule of an eye through a relatively small incision, as will be discussed hereinafter. Once positioned in the lens capsule of the eye, the lens skin 10 is inflated to its shape as shown in FIGS. 1 and 2 by inserting a liquid into the sac formed by the lens skin 10. The liquid is a flowable, polymerizable material which solidifies within the lens skin 10 to form an elastomeric filling 14 as shown in FIG. 2.

The unfilled lens skin 10, with the appended pair of tubes 12, is adapted to be rolled or folded into a small, elongate unit which can be inserted into the lens capsule of an eye through an incision which is no larger than about 3 or 4 millimeters, with the tubes 12 extending from the inserted lens skin back through the incision to the outside of the eye. An insertion member 16 which is advantageously used in inserting the lens skin 10 into the lens capsule of the eye is shown in FIG. 3 of the drawings.

The insertion member 16 comprises an elongate hollow sleeve 18 having first and second ends. The distal or second end of the hollow sleeve 18 has an elongate slot 20 formed in the sleeve 18 to extend inwardly from the second end thereof. The internal diameter of the hollow sleeve 18 is no greater than about 3 to 4 millimeters, and is adapted to receive the folded or rolled lens skin 10 therein. The slot 20 is adapted to receive the tubes 12 extending from the rolled or folded lens skin. The slot 20 has a width which is sufficient to receive the tubes 12 and has a depth of from about the equatorial diameter of the lens skin 10 when it is fully inflated to about 2.0 cm.

An elongated, inner shaft 22 having first and second ends is inserted into the first end of the hollow sleeve 18. The first end of the inner shaft 22 is inserted into the hollow sleeve 1 for sliding, telescopic movement within the hollow sleeve 18. The inner shaft 22 is sufficiently long that the first end thereof can be extended completely through the hollow sleeve 18 with the second end still extending from the first end of the hollow sleeve 18.

The second end of the hollow sleeve 18 is preferably flared inwardly into the hollow interior thereof as shown by the reference number 26 in the drawings. The flared inner end of the hollow sleeve 18 aids in the unfolding of the collapsed, folded lens skin 10 as the lens skin 10 is expelled from the hollow sleeve 18. A finger rest 28 in the form of a flange is preferably provided near the first end of the hollow sleeve 18, and a thumb pad 30 is also preferably provided adjacent to the second end of the inner shaft 22.

In using the system of the present invention, the empty lens skin 10 is rolled or folded into a generally cylindrical shape, with the tubes 12 extending generally from one end of the rolled or folded item. The rolled or folded lens skin 10 is then inserted lengthwise into the open second end of the hollow sleeve 18 of the insertion member 16, with the end of the folded unit from which the tubes 12 extend being the lead end which is slid into the hollow sleeve such that the tubes extend from the slot 20 in the hollow sleeve 18 generally adjacent to the inner end of the slot 20.

The end of the hollow sleeve 18 containing the folded lens skin 10 is then introduced into the eye 38 through a small (generally 3 to 4 millimeter) incision as shown in FIG. 5 of the drawings. The folded lens skin 10 is then ejected from the second end of the hollow sleeve 18 into the lens capsule 34 of the eye 38 through the capsulotomy used in the removal of the impaired lens material of the eye 38 by phacoemulsification or other small-incision techniques. The folded lens skin is ejected from the hollow sleeve 18 by pushing the inner shaft 22 through the hollow sleeve 18 thereby pushing the folded lens skin 10 from the second end of the hollow sleeve 18 and through the capsulotomy into the lens capsule 34 of the eye. The insertion member 16 is then withdrawn from the eye. The inserted lens skin 10 tends to unfold and assume an expanded, native shape within the lens capsule 34. The pair of tubes 28 extend through the capsulotomy in the lens capsule 34 and the incision in the eye 38 to the outside of the eye. Access to the interior of the sac formed by the injected lens skin 10 is provided through the pair of hollow, flexible tubes 12.

A flowable, liquid, polymerizable material, such as a monomer mixture or a prepolymer mixture, is injected through one of the pair of tubes 12 into the enclosed sac formed by the inserted lens skin 10 to inflate the lens skin 10 to substantially the shape of the biological content of the lens capsule 34 prior to the removal of such biological content from the lens capsule 34. Injecting and filling the inserted lens skin 10 is accomplished by means of a pump, gravity feed or a conventional syringe containing the injection fluid and attached to the filling tube of the pair of tubes 12 so that the filling fluid can be forced into the sac formed by the lens skin 10 inserted within the lens capsule 34 of the eye. As shown in FIG. 6, a conventional syringe 36 is advantageously used to inject the filling fluid into the lens skin 10 within the lens capsule of the eye.

Once the sac formed by the lens skin 10 within the lens capsule of the eye is filled, additional fluid is preferably flushed from the syringe or other source of the fluid through the feed tube and the inflated lens skin 10 to be discharged out the second of the pair of tubes 12. The second tube of the pair of tubes 12 in essence becomes a discharge tube for discharging air and flushing fluid from the inflated lens skin 10 positioned within the lens capsule 34 of the eye. To aid in the flushing of small air bubbles which adhere to the interior of the inflated lens skin 10, an evacuation probe 40 such as shown in FIG. 4 can be provided. The evacuation probe 40 comprises a rigid, elongate member having a curve 42. The curved end 42 of the evacuation probe 40 is adapted to be inserted into the sac formed by the inflated lens skin 10 within the lens capsule 34 of the eye through the discharge tube of the pair of tubes 12. During flushing of fluid through the inflated lens skin 10, the curved end 42 of the probe 40 is moved within the inflated lens skin 10 to dislodge air bubbles from the interior surface of the lens skin 10. The probe 40 is preferably made of a hollow tube itself, such that fluid can flow out of the probe 40 through the discharge tube of the pair of tubes 12. Thus, as an air bubble is dislodged by the probe 40, it is immediately flushed from the inflated lens skin 10 through the probe 40 and the discharge tube of the pair of tubes 12. An enlarged handle 44 is preferably provided adjacent to the end of the evacuation probe 40 opposite the curved end 42 for the surgeon to grasp as the probe 40 is being used.

When the inflated lens skin 10 is properly filled and all air bubbles have been flushed therefrom, each of the pair of tubes 12 is clamped and the liquid material in the inflated lens skin is allowed to polymerize to form the clear elastomeric material filling the inflated lens skin 10. The fluid material can be selected from a group of materials which when polymerized in turn forms a polymer selected from the group including silicones, acrylic hydrogels and urethanes. After the liquid material in the inflated lens skin 10 has polymerized, the pair of tubes 12 is carefully cut or otherwise removed from the surface of the lens skin 10 adjacent to the capsulotomy.

There are numerous advantages which are achieved by the novel system of the present invention. A few such advantages are:

The sac formed by the lens skin 10 fully contains the polymer injected into the eye and prevents any escape of the polymer or precursor liquid through nicks and tears which might not be detected in the lens capsule.

The attachment of the tubes 12 directly to the lens skin 10 eliminates the possibility of leakage of injected fluid into the eye.

The soft tubing used in the filling and evacuation tubes 12 mechanically decouples the implanted lens skin 10 from the surgeon's hand movements during the filling procedure. This makes the procedure much safer than if the surgeon were using a rigid injection instrument. It also allows the surgeon to designate an assistant to provide filling pressure if the surgeon wishes to devote his attention to eliminating bubbles from the injected material during filling.

The inserter 16 provides reliable introduction of the folded lens skin 10 through the small incision or capsulotomy. Because the lens emerges from the second end of the inserter 16 in a slow and controlled manner, the surgeon is able to verify that the lens is entering the desired location within the lens capsule.

The pair of tubes 12 provide for efficient flushing of air which is the only contaminant that can enter the inflated lens skin 10. Both air and excess fluid used in flushing the inflated lens skin 10 are vented well outside the eye. The evacuation probe allows the surgeon to be certain that all bubbles have been removed from the inflated lens skin 10 before curing of the liquid therein occurs.

The soft decoupling tubes 12 together with the external venting combine to allow for more latitude in physical properties and cure rates of the injected material. This is because a very low viscosity, slow-curing agent (which would be prone to leakage without the attached tubes) can be used to flush the inflated lens skin 10 and then be sealed in the lens skin 10 by use of clamps or similar means until the liquid has cured. This means that a wider range of filling materials are usable and that the surgeon need not maintain any instruments in position manually while the fluid material cures.

The closely controlled placement of the elastomeric, artificial lens within the lens capsule of the eye allows the ciliary apparatus s of the eye to deform the artificial lens in the same manner it does in a normal eye to provide much needed accommodation with the artificial lens.

Although preferred embodiments of the intraocular lens system of the present invention have been illustrated and described, it is to be understood that the present disclosure is made by way of example and that various other embodiments are possible without departing from the subject matter coming within the scope of the following claims, which subject matter is regarded as the invention.

I claim:

1. An inflatable, intraocular lens for implantation within the lens capsule of an eye following removal of the biological contents of the lens capsule, said lens comprising a thin-walled lens skin forming a substantially enclosed, collapsible sac, said lens skin being made of a clear, flexible polymeric material and having a wall thickness no greater than about 0.15 millimeter, said lens skin further having an exterior shape when inflated which is substantially the same as the shape of the biological content of the lens capsule of a normal eye; and a pair of longitudinal, flexible tubes extending from said lens skin, with the lumen of each tube communicating with the inside of said sac formed by said lens skin, wherein said lens skin, when in a collapsed, folded condition, can be inserted into the lens capsule of an eye through a relatively small incision in the eye, with said lens skin being adapted to be inflated through the pair of tubes after said lens skin has been inserted into said lens capsule of the eye to substantially the shape of the biological content of the lens capsule prior to the removal of such biological content from said lens capsule.

2. An inflatable, intraocular lens in accordance with claim 1, wherein a clear elastomeric material fills the sac formed by the lens skin to give the lens skin its inflated shape, said elastomeric material being injected, in the form of a flowable, liquid, polymerizable material through one of said pair of tubes into the enclosed sac formed by said lens skin, with air bubbles and excess liquid material being flushed from the inflated lens skin through the other of said pair of tubes, wherein the liquid material polymerizes within the inflated lens skin to form said clear elastomeric material filling said sac formed by said lens skin.

3. An inflatable, intraocular lens in accordance with claim 2, wherein following the injection of the elastomeric material into the sac formed by the lens skin, the pair of elongate, flexible tubes are carefully removed from the inflated surface of said lens skin.

4. An inflatable, intraocular lens in accordance with claim 1, wherein said lens skin has a wall thickness that varies over the area of said lens skin in a predetermined pattern but never exceeds 0.15 millimeters.

5. An intraocular lens system comprising the inflatable, intraocular lens in accordance with claim 1 and further including an insertion member for inserting said lens skin, when in a collapsed, folded condition, into the lens capsule of an eye through a relatively small incision in the eye, said insertion member comprising an elongate hollow sleeve having a first and second end, with the second end further having an elongate slot formed in the hollow sleeve to extend inwardly from said second end of said hollow sleeve;

an elongate, inner shaft having a first and second end, with the first end of said inner shaft being inserted into said hollow sleeve for sliding, telescopic movement within said hollow sleeve, said inner shaft being sufficiently long that the first end thereof can be extended completely through said hollow sleeve with the second end still extending from the first end of said hollow sleeve, whereby the collapsed, folded lens skin can be received within the hollow second end of said hollow sleeve, with the pair of flexible tubes on said lens skin extending from said collapsed, folded lens skin within said hollow sleeve through said elongate slot in the second end of said hollow sleeve, and further wherein following insertion of the second end of said hollow sleeve containing the collapsed, folded lens skin into the eye, the inner shaft is slid through the hollow sleeve by pushing on the second end of said inner shaft so as to expel the lens skin from the first end of said hollow sleeve into the lens capsule of the eye.

6. An intraocular lens system in accordance with claim 5, wherein the second end of said hollow sleeve is flared inwardly into the hollow interior thereof to aid in the unfolding of the collapsed, folded lens skin as said lens skin is expelled from said hollow sleeve.

7. An intraocular lens system in accordance with claim 6, wherein a finger rest flange is provided near the first end of said hollow sleeve, and a thumb pad is provided adjacent to the second end of said inner shaft.

8. An intraocular lens system in accordance with claim 5, further including an evacuation probe comprising a rigid, elongate member having a curve at one end thereof, wherein the curved end of the evacuation probe can be inserted into the sac formed by said lens skin through one of the tubes extending from the lens skin during the injection of the liquid material into said sac, with the curved end of said evacuation probe being used to dislodge air bubbles from the interior surface of said sac so that the air bubbles can be flushed with excess liquid material from said sac.

9. An intraocular lens system in accordance with claim 8, wherein the evacuation probe is rigid, hollow tube open at both of its ends to allow liquid material and air bubbles to be flushed therethrough.

10. An intraocular lens system in accordance with claim 8, wherein an enlarged handle section is provided adjacent to the end of the evacuation probe opposite the curved end.

11. A method of implanting an inflatable, intraocular lens within the lens capsule of an eye following removal of the biological contents of the lens capsule, said method comprising folding an inflatable, intraocular lens made in accordance with claim 1 into a small unit which can be inserted into a relatively small incision in the eye;

inserting the folded lens skin of said lens into the lens capsule of an eye through a relatively small incision in the lens capsule, such that the pair of tubes on the lens skin of said lens extends outwardly from said lens capsule through the relatively small incision;

allowing the folded lens skin to expand within the lens capsule;

injecting a flowable, liquid, polymerizable material through one of said pair of tubes into the enclosed sac formed by said lens skin to inflate the lens skin to substantially the shape of the biological content of the lens capsule prior to the removal of such biological content from said lens capsule;

flushing the inflated lens skin with excess liquid material and expelling the excess liquid material together with air bubbles through the other of said pair of tubes until all air bubbles are flushed from the inflated lens skin;

clamping each of the tubes of the pair of tubes and allowing the liquid material in the inflated lens skin to polymerize and form said clear elastomeric material filling said inflated lens skin; and after the liquid material has polymerized in said inflated lens skin, carefully removing the pair of tubes from said inflated lens skin.

12. A method of implanting an inflatable, intraocular lens within the lens capsule of an eye in accordance with claim 11 wherein an evacuation probe in accordance with claim 8 is inserted through the other of said pair of tubes during the step in which excess liquid fluid is being flushed through said inflated lens skin, with the evacuation probe being manually manipulated to dislodge air bubbles from the interior surface of the inflated lens skin.

* * * * *